(12) United States Patent
Ter-Martirosyan et al.

(10) Patent No.: US 11,795,652 B2
(45) Date of Patent: Oct. 24, 2023

(54) METHOD OF COMPACTION OF BASES COMPOSED OF WEAK MINERAL SOILS

(71) Applicants: JOINT STOCK COMPANY "ROSENERGOATOM", Moscow (RU); JOINT STOCK COMPANY "SCIENCE AND INNOVATIONS", Moscow (RU)

(72) Inventors: Zaven Grigor'evich Ter-Martirosyan, Moscow (RU); Armen Zavenovich Ter-Martirosyan, Moscow (RU); Anatoliy Yur'evich Mirniy, Moscwo (RU); Evgeniy Stanislavovich Sobolev, Moscow (RU); Vitaliy Valentinovich Sidorov, Tverskaya oblast' (RU); Georgiy Olegovich Anzhelo, Moscow (RU); Ivan Nikolaevich Luzin, Bashkortostan (RU)

(73) Assignees: Joint Stock Company Rosenergoatom, Moscow (RU); Joint Stock Company "Science and Innovations", Moscow (RU)

( * ) Notice: Subject to any disclaimer, the term of this patent is extended or adjusted under 35 U.S.C. 154(b) by 878 days.

(21) Appl. No.: 16/309,078

(22) PCT Filed: Dec. 8, 2017

(86) PCT No.: PCT/RU2017/000916
§ 371 (c)(1),
(2) Date: Dec. 11, 2018

(87) PCT Pub. No.: WO2019/066680
PCT Pub. Date: Apr. 4, 2019

(65) Prior Publication Data
US 2023/0082840 A1     Mar. 16, 2023

(30) Foreign Application Priority Data

Sep. 29, 2017 (RU) .......................... RU2017133868

(51) Int. Cl.
*E02D 27/26* (2006.01)
*G01N 33/24* (2006.01)

(52) U.S. Cl.
CPC .............. *E02D 27/26* (2013.01); *G01N 33/24* (2013.01); *E02D 2300/0079* (2013.01)

(58) Field of Classification Search
CPC ......... E02D 27/26; E02D 27/28; E02D 1/022; E02D 2600/0079; G01N 33/24
See application file for complete search history.

(56) References Cited

U.S. PATENT DOCUMENTS

2017/0058477 A1\*  3/2017  Niroumand ............... E02D 3/08

FOREIGN PATENT DOCUMENTS

| KR | 20190043709 A | * | 4/2019 |
| KR | 20210065509 A | * | 6/2021 |
| RU | 2473741 C2 | * | 1/2013 |

\* cited by examiner

*Primary Examiner* — Kyle Armstrong
(74) *Attorney, Agent, or Firm* — Dentons US LLP

(57) ABSTRACT

Methods for strengthening soils under bases and foundations of buildings and structures with compaction of the base composed of weak mineral soils by determining the optimal design process parameters of the ground piles over the entire area of the base. The essence of the invention is that the method of compaction of bases composed of weak mineral soils that includes formation of a well, filling each well with the compacting material, and creation of a compacting effect on the compacting material by the hollow tubular working tool to form a ground pile. Preliminary engineering and geological surveys of the base area is performed to determine the values of the modulus of deformation, the Poisson's ratio, the internal friction angle, the specific cohesion, the specific gravity, and the initial void ratio of the weak mineral soil.

5 Claims, No Drawings

METHOD OF COMPACTION OF BASES COMPOSED OF WEAK MINERAL SOILS

CROSS-REFERENCE TO RELATED APPLICATIONS

This application is a US 371 Application from PCT/RU2017/000916 filed Dec. 8, 2017, which claims priority to Russia Application 2017133868 filed Sep. 29, 2017, the technical disclosures of which are hereby incorporated herein by reference.

The invention relates to construction, in particular to methods for strengthening soils under bases and foundations of buildings and structures, including electric power industry facilities.

As concerns designing of bases and foundations of buildings and structures, weak water-saturated clay soils with low deformability and strength characteristics lie quite often in a selected area of construction. In such cases, the transformation of the weak base is carried out by various methods that lead to compaction and hardening of the initially weak soil. Soils can be compacted by rolling, tamping, injecting various compounds, or by applying various technologies of ground piles.

There is known a method to strengthen that includes drilling a well, loosening the soil of this well walls, and applying a strengthening effect on this soil (author's certificate for the patent USSR No. 708010, 30.09.77). In this method, the strengthening effect is created only on the soil, which is loosened from the walls of the well. Once this soil is compacted, a certain degree of strengthening is achieved, which can not be increased any more.

This method does not allow the required degree of soil strengthening for the foundations for modern construction.

The closest analogue is the method of compaction of soil (patent for invention of the Russian Federation No. 2473741), which includes formation of a well, filling the well with the compacting material, and creation of a compacting effect on the compacting material by the hollow tubular working tool to form a ground pile.

The disadvantage of the closest analogue is the lack of calculations for the selection of technological parameters of compaction of the ground pile depending on soil properties, reconciliation of the values obtained after compaction with design ones, which leads to the need for additional soil compaction operations and selection of the required number of wells.

The object of the proposed invention is to increase the productivity of soil compaction, reduce the material consumption and labour intensity.

The technical result achieved by this invention consists in compaction of the base composed of weak mineral soils by determining the optimal design process parameters of the ground piles over the entire area of the base.

The essence of the invention is that the method of compaction of bases composed of weak mineral soils that includes formation of a well, filling each well with the compacting material, and creation of a compacting effect on the compacting material by the hollow tubular working tool to form a ground pile, proposes to perform preliminary engineering and geological surveys of the base area and determine the values of the modulus of deformation, the Poisson's ratio, the internal friction angle, the specific cohesion, the specific gravity, the initial void ratio of the weak mineral soil, set the required design modulus of deformation of the layer to be compacted, then, taking the value $\varepsilon_i$ of expansion deformation of each well equal to 0.1, calculate the void ratio of the weak mineral soil after compaction around the ground pile $e_i$, according to the formula:

$e_i = e_0 - (1+e_0) \cdot \varepsilon_i$, where $e_i$ is the void ratio of the weak mineral soil after compaction around the ground pile;

$e_0$ is the initial void ratio of the weak mineral soil to be compacted;

$\varepsilon_i$ is the accepted value of the expansion deformation of the well, and determine the predicted value of the liquidity index of the weak mineral soil at each step by the formula:

$$I_{L2} = I_{L1} \cdot \left( \frac{\frac{e_2}{e_1} \cdot w_1 - w_p}{w_1 - w_p} \right),$$

where $I_{L1}$ is the value of the liquidity index of the weak mineral soil in natural conditions;

$I_{L2}$ is the value of the liquidity index of the weak mineral soil after compaction;

$e_1$ is the value of the void ratio of the weak mineral soil in natural conditions;

$e_2$ is the value of the void ratio of the weak mineral soil after compaction;

$w_1$ is the moisture of the weak mineral soil in natural conditions;

$w_p$ is the plastic limit of the weak mineral soil, then, based on the known normative values, take the nearest preliminary value of the modulus of deformation $E^z$ of the mineral soil surrounding the ground pile depending on the obtained values of the void ratio of the weak mineral soil after compaction around the ground pile $e_i$ and the soil liquidity index after compaction $I_{L2}$, then take the spacing of the ground piles equal to three diameters of the hollow tubular working tool and determine the value of the actual average reduced modulus of deformation of the base by the formulae:

$$\bar{E} = \beta/\bar{m}, \quad \bar{m} = \frac{m_c \cdot \bar{m}_z}{\bar{m}_z \cdot \varepsilon + m_c(1-\varepsilon)}, \quad \bar{m}_z = \frac{\beta}{E_z}, \quad m_c = \frac{\beta}{E_c}, \quad \varepsilon = \frac{a^2}{b^2},$$

where $\bar{E}$ is the actual average reduced modulus of deformation of the base;

$\beta$ is the coefficient of lateral expansion equal to 0.8 for a composite soil body;

$m_z$ is the coefficient of volume change of the soil;

$m_c$ is the coefficient of volume change of the ground pile material;

$\bar{m}$ is the coefficient of volume change of the body consisting of the ground pile and soil surrounding it;

$E^z$ is the modulus of deformation of the mineral soil surrounding the ground pile;

$E_c$ is the modulus of deformation of the ground pile material;

$\varepsilon$ is the value of the volumetric strain of the mineral soil being compacted during the well expansion;

a is the final radius of the ground pile;

b is the radius of the body consisting of the ground pile and soil surrounding it equal to half the design spacing of the ground piles, compare it with the design modulus of deformation of the mineral soil and, if the actual average reduced modulus of deformation of the base soil is smaller than the one provided for by the design, increase the well expansion deformation value ci iteratively in increments of 0.1 and repeat the calculation of the actual average reduced modulus of deformation of the base until the design value is reached or spacing of the ground piles is equal to the value of 1.5 times of the diameter of the hollow tubular working tool, wherein the increase of the well radius corresponding to the value of the accepted expansion deformation during piling is calculated by the formula:

$$r_p = R\sqrt{\varepsilon}, \text{ where}$$

$r_p$ is the extended well radius;
R is the radius of influence of one ground pile equal to half the spacing of the ground piles;
ε is the value of the volumetric strain of the soil being compacted during the well expansion,
the length of the ground pile is taken equal to the distance from the roof to the sole of at least one layer requiring compaction, then drill the well corresponding to the ground pile length by insertion of a hollow tubular working tool, feeding the compacting material into the well through a cavity of a hollow tubular working tool; the compacting effect for formation of a ground pile is carried out by insertion of a hollow tubular working tool into the compacting material; then, perform additional engineering and geological surveys on the area of the base to determine the modulus of deformation of the compacted mineral soil between the ground piles; calculate the actual average reduced modulus of deformation of the compacted base and compare it with the design value; and if the actual average reduced modulus of deformation of the base does not correspond to the design value, install additional ground piles between previously installed ones.

It is also proposed to advantageously cover the lower end of the hollow tubular working tool with a damper or an expendable bottom before it is pressed into the soil of the base; and after filling the cavity of the hollow tubular working tool with the compacting material, open the damper of the hollow tubular working tool to spill the compacting material into the well, raise the hollow tubular working tool to a given height of the compacting layer, and insert the hollow tubular working tool into the compacting material; repeat the pressing of the compacting material in layers to the entire length of the ground pile to achieve the desired compaction of the weak mineral soil.

As a compacting material, it is possible to use crushed stone, and/or sand, and/or gravel, and/or inert material; the hollow tubular working tool is proposed to be symmetric with respect to its central axis.

A distinctive feature of the claimed method is that, based on the results of engineering and geological surveys, the initial parameters of the weak mineral soil are determined by the area of the base, with the use of which the calculations are carried out to select the technological parameters for compaction of ground piles (the spacing and radius of the extended well) all over the base. After compaction of the base, reconciliation of the obtained parameter of compacted soil on the base as a whole with the design allows to determine the sufficiency of the number of installed ground piles. Insertion of the hollow tubular working tool into the base soil allows the first compaction of a weak mineral soil. Overlapping of the lower end of the working tool with a damper or an expendable bottom allows the pressing of the compacting material in the well. Insertion of the working tool into the compacting material in layers allows to significantly expand the well, form a ground pile and compact the soil around the ground pile in the radial (with respect to the ground pile) direction. Compaction of the soil surrounding the ground pile also causes activation of the consolidation process due to the appearance of excessive pore pressure. The use of crushed stone, and/or sand, and/or gravel, and/or any other inert material as a compacting material allows to form a ground pile with the necessary characteristics, depending on the properties of the weak mineral soil being compacted in a way to prevent the particles of the compacted soil from penetrating through the ground pile body.

The use of a hollow tubular tool symmetrical with respect to the central axis allows a uniform radial compaction of the base soil.

The claimed method is performed as follows.

As initial data on the results of standard engineering and geological surveys, the physical and mechanical characteristics of the base soils are determined, namely the values of the modulus of deformation, the Poisson's ratio, the internal friction angle, the specific cohesion, the specific gravity, the initial void ratio of the weak mineral soil.

Then, the required design modulus of deformation of the soil layer being compacted is set, and taking the value of the expansion deformation $\varepsilon_i$ of each well equal to 0.1, the void ratio of the weak mineral soil after compaction around the ground pile $e_i$ is calculated by the formula:

$$e_i = e_0 - (1 + e_0) \cdot \varepsilon_i, \text{ where}$$

$e_i$ is the void ratio of the weak mineral soil after compaction around the ground pile;
$e_0$ is the initial void ratio of the weak mineral soil to be compacted;
$\varepsilon_i$ is the accepted value of the expansion deformation of the well.

Next, the predicted value of the liquidity index of the weak mineral soil is determined at each step by the formula:

$$I_{L2} = I_{L1} \cdot \left( \frac{\frac{e_2}{e_1} \cdot w_1 - w_p}{w_1 - w_p} \right),$$

where
$I_{L1}$ is the value of the liquidity index of the weak mineral soil in natural conditions;
$I_{L2}$ is the value of the liquidity index of the weak mineral soil after compaction;
$e_1$ is the value of the void ratio of the weak mineral soil in natural conditions;
$e_2$ is the value of the void ratio of the weak mineral soil after compaction;
$w_1$ is the moisture of the weak mineral soil in natural conditions;
$w_p$ is the plastic limit of the weak mineral soil.

Then, according to the known nonnative values (for example, from Table B.4 of SP 22.13330.2011), the nearest preliminary value of the modulus of deformation $E^z$ of the mineral soil surrounding the ground pile is obtained, depending on the obtained values of the void ratio of the weak mineral soil after compaction around the ground pile $e_i$ and the soil liquidity index after compaction $I_{L2}$. Then, the spacing of the ground piles is taken equal to the three diameters of the hollow tubular working tool.

Such a spacing of the ground piles is taken from the following assumptions:

at a spacing of the ground piles less than three diameters of the hollow tubular working tool, it is assumed that the influence of some ground piles on adjacent ones in the course of expansion is significant, which may result in the displacement of a part of adjacent ground piles in the horizontal direction (leading to their deviation from the vertical position) and lead to improper compaction of the base;

at a spacing of the piles more than three diameters of the hollow tubular working tool, there is a possibility of appearance of undercompacted zones between the ground piles.

Next, the value of the actual average reduced modulus of deformation of the base is determined by formulae:

$$\overline{E} = \beta/\overline{m}, \overline{m} = \frac{m_c \cdot m_z}{m_z \cdot \varepsilon + m_c(1-\varepsilon)}, m_z = \frac{\beta}{E_z}, m_c = \frac{\beta}{E_c}, \varepsilon = \frac{a^2}{b^2},$$

where $\overline{E}$ is the actual average reduced modulus of deformation of the base;

B is the coefficient of lateral expansion equal to 0.8 for a composite soil body;

$m_z$ is the coefficient of volume change of the soil;

$m_c$ is the coefficient of volume change of the ground pile material;

$\overline{m}$ is the coefficient of volume change of the body consisting of the ground pile and soil surrounding it;

$E_z$ is the modulus of deformation of the mineral soil surrounding the ground pile;

$E_c$ is the modulus of deformation of the ground pile material;

$\varepsilon$ is the value of the volumetric strain of the mineral soil being compacted during the well expansion;

a is the final radius of the ground pile;

b is the radius of the body consisting of the ground pile and soil surrounding it equal to half the design spacing of the ground piles.

The obtained value of the actual average reduced modulus of deformation of the base is compared with the design modulus of deformation of the mineral soil and, if the actual average reduced modulus of deformation of the base soil is smaller than the one provided for by the design, the well expansion deformation value $\varepsilon_i$ is increased iteratively in increments of 0.1, and the calculation of the actual average reduced modulus of deformation of the base is repeated until the design value is reached or spacing of the ground piles is equal to the value of 1.5 times of the diameter of the hollow tubular working tool.

Wherein the increase of the well radius corresponding to the value of the accepted expansion deformation during piling is calculated by the formula:

$$r_p = R\sqrt{\varepsilon}, \text{ where}$$

$r_p$ is the extended well radius;

R is the radius of influence of one ground pile equal to half the spacing of the ground piles;

$\varepsilon$ is the value of the volumetric strain of the soil being compacted during the well expansion.

The length of the ground pile requiring compaction is taken equal to the distance from the roof to the sole of at least one layer; wherein ground piles are installed for the entire propagation of weak water-saturated soils with a modulus of deformation of less than 10 MPa, the mechanical characteristics of which need to be increased. To determine the length of the ground piles, the depth of the compressible layer is preliminarily determined according to the standard method SP 22.13330.2011. If the lower boundary of the compressible strata falls into soils with a modulus of deformation of less than 10 MPa, it is recommended to install ground piles for its entire capacity. If possible, the length of the ground pile shall be selected so that its lower end abuts the soil with sufficiently high mechanical characteristics. With a non-horizontal bedding of stratum superface (strong and relatively poorly deformed pound), the length of the ground piles shall be assigned so that all lower ends of the compaction elements are guaranteed to be immersed in it in not less than 0.5 in.

Then, the well is drilled corresponding to the length of the ground pile by immersing the hollow working tool. Wherein the lower end of the working tool is covered with a damper before it is immersed into the base soil; and after filling the compacting material into the cavity of the working tool, the damper of the working tool is opened to spill the compacting material into the well; the working tool is raised to the set height of the compacting layer, after which the tool is pressed into the compacting material. The pressing of the compacting material is repeated in layers to the entire length of the column to achieve the desired compaction of the weak mineral soil.

It is also possible to overlap the lower end of the working tool with an expendable bottom.

As a compacting material, it is possible to use crushed stone, and/or sand, and/or gravel, and/or inert material. Wherein in this case, sandy and coarse clastic soils with water permeability parameters that are considerably higher than the parameters of the compacted weak soil, can be used as a material for compaction ground piles. The deformation properties of the material of the compaction ground pile after its pressing into the well are determined by the required reduced modulus of deformation at the construction site.

When installing ground piles in soils, in which mechanical suffusion is likely to occur, it is necessary to consider the use of crushed stone and sand as a material for ground piles, the composition of which is selected in such a way to prevent the particles of the compacted soil from penetrating through its body.

At the installation of ground piles in clay soils, it is also recommended to use crushed stone and sand mixture to reduce the rate of development of the colmatation process of the ground pile body.

The working tool used is usually chosen to be symmetrical with respect to its central axis. When using a square working tool (or with a section in the form of any regular polygon with a number of sides greater than four), the shape of the pile of increased radius will also be close to the circle. All calculations are performed for the circular pile model in accordance with the presented method. In practice, if a square working tool is required, a square cross section with an area equal to or greater than the circular cross-section area is taken. This is necessary for the equality of volumes of filled and compacted material in the well.

Then, additional engineering and geological surveys are performed on the base area to determine the modulus of deformation of the compacted mineral soil between the ground piles; and the actual average reduced modulus of deformation of the compacted base is calculated and compared with the design value. If the actual average reduced modulus of deformation of the base does not correspond to the design value, additional ground piles are installed between previously installed ones.

Using the proposed method, it is possible to design and carry out compaction of the bases of buildings and structures of increased criticality at the selected construction site in accordance with the specified design values without additional costs.

The invention claimed is:

1. The method of compaction of bases composed of weak mineral soils that includes formation of a well, filling each well with the compacting material, and creation of a compacting effect on the compacting material by the hollow tubular working tool to form a ground pile, wherein engineering and geological surveys of the base area are previously performed, and the values of the modulus of deformation, the Poisson's ratio, the internal friction angle, the specific cohesion, the specific gravity, the initial void ratio of the weak mineral soil are determined; the required design modulus of deformation of the layer to be compacted is set; then, taking the value $\varepsilon_i$ of expansion deformation of each well equal to 0.1, the void ratio of the weak mineral soil after compaction around the ground pile $e_i$ is calculated according to the formula:

$$e_i = e_0 - (1+e_0)\cdot\varepsilon_i, \text{ where}$$

$e_i$ is the void ratio of the weak mineral soil after compaction around the ground pile;

$e_0$ is the initial void ratio of the weak mineral soil to be compacted;

$\varepsilon_i$ is the accepted value of the expansion deformation of the well, and the predicted value of the liquidity index of the weak mineral soil is determined at each step by the formula:

$$I_{L2} = I_{L1} \cdot \left( \frac{\frac{e_2}{e_1} \cdot w_1 - w_p}{w_1 - w_p} \right),$$

where $I_{L1}$ is the value of the liquidity index of the weak mineral soil in natural conditions;

$I_{L2}$ is the value of the liquidity index of the weak mineral soil after compaction;

$e_1$ is the value of the void ratio of the weak mineral soil in natural conditions;

$e_2$ is the value of the void ratio of the weak mineral soil after compaction;

$w_1$ is the moisture of the weak mineral soil in natural conditions;

$w_p$ is the plastic limit of the weak mineral soil, then, based on the known nonnative values, take the nearest preliminary value of the modulus of deformation $E_z$ of the mineral soil surrounding the ground pile depending on the obtained values of the void ratio of the weak mineral soil after compaction around the ground pile $e_i$ and the soil liquidity index after compaction $I_{L2}$, then take the spacing of the ground piles equal to three diameters of the hollow tubular working tool and determine the value of the actual average reduced modulus of deformation of the base by the formulae:

$$\bar{E} = \beta/\bar{m},\ \bar{m} = \frac{m_c \cdot m_{z}}{m_{z} \cdot \varepsilon + m_c(1-\varepsilon)},\ m_{z} = \frac{\beta}{E_z},\ m_c = \frac{\beta}{E_c},\ \varepsilon = \frac{a^2}{b^2},$$

where $\bar{E}$ is the actual average reduced modulus of deformation of the base;

$\beta$ is the coefficient of lateral expansion equal to 0.8 for a composite soil body;

$m_z$ is the coefficient of volume change of the soil;

$m_c$ is the coefficient of volume change of the ground pile material;

$\bar{m}$ is the coefficient of volume change of the body consisting of the ground pile and soil surrounding it;

$E_z$ is the modulus of deformation of the mineral soil surrounding the ground pile;

$E_c$ is the modulus of deformation of the ground pile material;

$\varepsilon$ is the value of the volumetric strain of the mineral soil being compacted during the well expansion;

a is the final radius of the ground pile;

b is the radius of the body consisting of the ground pile and soil surrounding it equal to half the design spacing of the ground piles, it is compared with the design modulus of deformation of the mineral soil and, if the actual average reduced modulus of deformation of the base soil is smaller than the one provided for by the design, the well expansion deformation value $\varepsilon_i$ is increased iteratively in increments of 0.1, and the calculation of the actual average reduced modulus of deformation of the base is repeated until the design value is reached or spacing of the ground piles is equal to the value of 1.5 times of the diameter of the hollow tubular working tool, wherein the increase of the well radius corresponding to the value of the accepted expansion deformation during piling is calculated by the formula:

$$r_p = R\sqrt{\varepsilon}, \text{ where}$$

$r_p$ is the extended well radius;

R is the radius of influence of one ground pile equal to half the spacing of the ground piles;

$\varepsilon$ is the value of the volumetric strain of the soil being compacted during the well expansion, the length of the ground pile requiring compaction is taken equal to the distance from the roof to the sole of at least one layer; then the well corresponding to the ground pile length is drilled by insertion of a hollow tubular working tool; the compacting material is fed into the well through a cavity of a hollow tubular working tool; the compacting effect for formation of a ground pile is carried out by insertion of a hollow tubular working tool into the compacting material; then, additional engineering and geological surveys are performed on the area of the base to determine the modulus of deformation of the compacted mineral soil between the ground piles;

the actual average reduced modulus of deformation of the compacted base is calculated and compared with the design value; and if the actual average reduced modulus of deformation of the base does not correspond to the design value, additional ground piles are installed between previously installed ones.

2. The method of compaction of bases according to claim 1, wherein the lower end of the hollow tubular working tool is overlapped with a damper or an expendable bottom before it is pressed into the base soil.

3. The method of compaction of bases according to claim 2, wherein after filling the cavity of the hollow tubular working tool with the compacting material, the damper of the hollow tubular working tool is opened to spill the compacting material into the well; the hollow tubular working tool is raised to a given height of the compacting layer; the hollow tubular working tool is inserted into the compacting material; the pressing of the compacting material is repeated in layers to the entire length of the ground pile to achieve the desired compaction of the weak mineral soil.

4. The method of compaction of bases according to claim 1, wherein crushed stone, and/or sand, and/or gravel, and/or inert material is used as a compacting material.

5. The method of compaction of bases according to claim 1, wherein the hollow tubular working tool is symmetric with respect to its central axis.

\* \* \* \* \*